(12) United States Patent
Kobayashi

(10) Patent No.: US 10,952,781 B2
(45) Date of Patent: Mar. 23, 2021

(54) CABLE SADDLE

(71) Applicant: DePuy Synthes Products, Inc., Raynham, MA (US)

(72) Inventor: Kenneth I. Kobayashi, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 561 days.

(21) Appl. No.: 15/818,262

(22) Filed: Nov. 20, 2017

(65) Prior Publication Data

US 2018/0161083 A1 Jun. 14, 2018

Related U.S. Application Data

(60) Provisional application No. 62/431,638, filed on Dec. 8, 2016.

(51) Int. Cl.
| | |
|---|---|
| *A61B 17/82* | (2006.01) |
| *A61B 17/80* | (2006.01) |
| *A61B 17/84* | (2006.01) |
| *A61B 17/74* | (2006.01) |

(52) U.S. Cl.
CPC ............ *A61B 17/82* (2013.01); *A61B 17/809* (2013.01); *A61B 17/74* (2013.01); *A61B 17/8085* (2013.01); *A61B 17/842* (2013.01)

(58) Field of Classification Search
CPC ... A61B 17/74; A61B 17/8085; A61B 17/809; A61B 17/82; A61B 17/842; A61B 17/8861
See application file for complete search history.

(56) References Cited

U.S. PATENT DOCUMENTS

| | | | | |
|---|---|---|---|---|
| 5,190,545 | A * | 3/1993 | Corsi ..................... | A61B 17/82 606/309 |
| 5,665,089 | A * | 9/1997 | Dall ....................... | A61B 17/80 606/309 |
| 8,672,969 | B2 * | 3/2014 | Stone .................. | A61B 17/8685 606/232 |

(Continued)

FOREIGN PATENT DOCUMENTS

| | | |
|---|---|---|
| KR | 101625177 | 6/2016 |
| WO | 2016/032273 | 3/2016 |

*Primary Examiner* — Anu Ramana
(74) *Attorney, Agent, or Firm* — Fay Kaplun & Marcin, LLP

(57) ABSTRACT

The present embodiments include a cable cerclage system and method for the correction of fractures. The system and method can include a cable saddle including first and second loops extending from an upper surface thereof, the first and second loops including apertures extending therethrough and sized and shaped to receive a cerclage cable therethrough. The present embodiments are also directed to a cable cerclage system including at least one cable link, the cable link having a through-hole extending therethrough from a first end to a second end and including a first coupling member at a first and a second coupling member at a second end. The first coupling member of a first cable link is configured to couple to the second coupling member of an adjacent second cable link so that the through-holes of the first and second cable links align to form an elongated cerclage cable passageway.

13 Claims, 6 Drawing Sheets

(56) References Cited

U.S. PATENT DOCUMENTS

| | | | |
|---|---|---|---|
| 2006/0167456 A1* | 7/2006 | Johnston | A61B 17/1728 |
| | | | 606/86 B |
| 2006/0235406 A1* | 10/2006 | Silverman | A61B 17/80 |
| | | | 606/71 |
| 2014/0243907 A1 | 8/2014 | Cavallazzi et al. | |
| 2014/0277176 A1* | 9/2014 | Buchanan | A61B 17/8014 |
| | | | 606/281 |

* cited by examiner

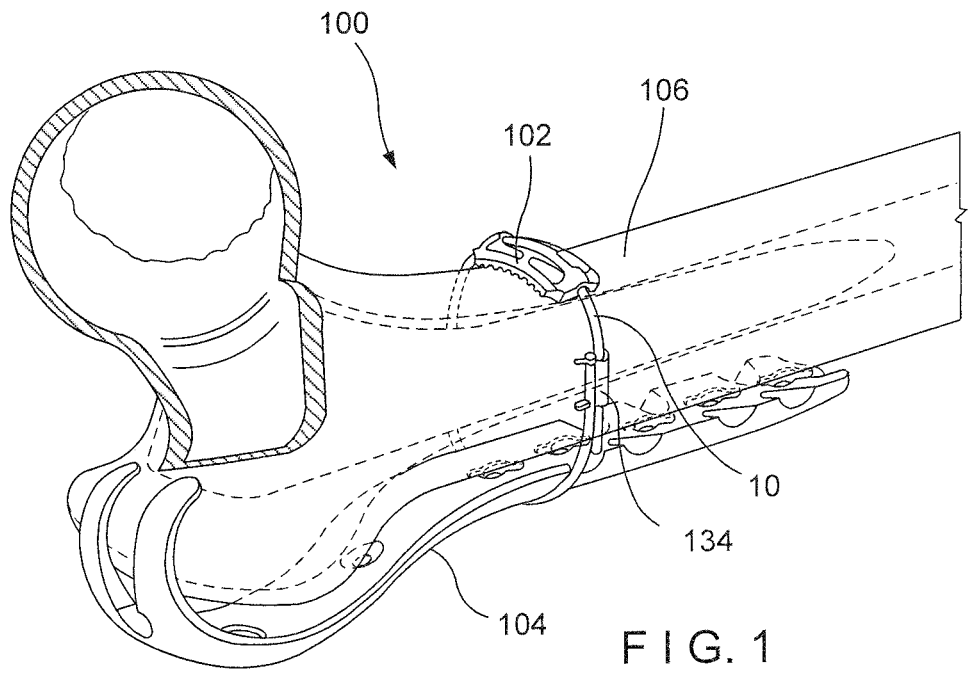
FIG. 1
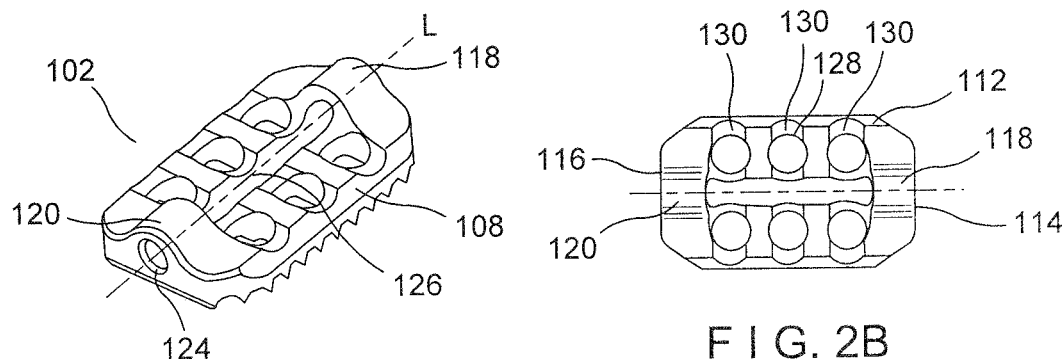
FIG. 2A
FIG. 2B
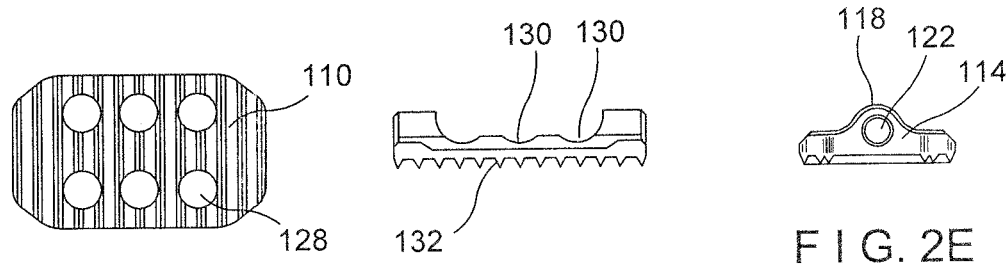
FIG. 2C
FIG. 2D
FIG. 2E

CABLE SADDLE

PRIORITY CLAIM

The present application claims priority to U.S. Provisional Patent Application Ser. No. 62/431,638 filed on Dec. 8, 2016. The entire disclosure of the above application is expressly incorporated herein by reference

BACKGROUND

Bones are often treated using cerclage techniques in which a wire or other cable is wrapped around a portion of bone to facilitate fixation or repair thereof. Cerclage procedures generally involve looping a wire or cable around the bone to be repaired. In some cases, typically in periprosthetic fractures, the cable has a tendency to subside into osteoporotic bone, causing the loosening of the overall construct. In these instances, it may be necessary to replace the wire or cable with a new cable system. Sometimes these procedures have to be repeated with second or third replacement procedures being required. Thus, there is a need for a cable instrument or implant that prevents cerclage cables from subsiding into bone while offering a value-added upgrade to existing customers who may not be willing to undergo replacement of a subsided cable with a completely new cabling system.

SUMMARY

The present embodiments relate to a cerclage system and method for stabilizing fractures using either a cable saddle or a cable belt in addition to a cerclage cable.

In one aspect, a fracture stabilization device according to an exemplary embodiment includes a body extending from a first end to a second end along a longitudinal axis, the body defining an upper surface and a bone facing surface and including a first loop extending from the surface at the first end and a second loop extending from the upper surface a second end. The first and second loops include apertures extending therethrough sized and shaped to receive a cerclage cable therethrough. The upper surface includes a plurality of elongated reliefs extending transverse to the longitudinal axis of the body to facilitate bending of the body along its longitudinal axis to conform to a contour of a target portion of bone over which the fracture stabilization device is to be mounted. In one embodiment, the upper surface includes a groove extending from the first loop to the second loop and open to the apertures. In another embodiment, the bone facing surface includes a plurality of ridges. In a further embodiment the body includes a plurality of holes extending from the bone facing surface to the upper surface. In yet another embodiment, the plurality of reliefs is open to at least one of the plurality of holes.

In another aspect, a system for securing a target portion of bone includes an elongated cerclage cable extending from a proximal end to a distal end and configured to circle the target portion of bone. The system also includes a cable link comprising an upper surface and a bone-facing surface and extending from a first end to a second end. The cable link includes a through-hole extending therethrough from the first end to the second end, the through-hole sized and shaped to receive the cerclage cable therethrough. The first end includes a first coupling member and the second end includes a second coupling member such that the first coupling member of a first cable link is configured to couple to the second coupling member of an adjacent second cable link so that the through-holes of the first and second cable links align to form an elongated cerclage cable passageway. In an embodiment, the first coupling member includes a rounded protrusion configured to be slidably received by the second coupling member. In another embodiment, the second coupling member is formed as a C-shaped extension configured to slidably receive the first coupling member therein. In a further embodiment, the bone-facing surface includes a plurality of ridges. In a further embodiment, the system includes an elongated bone plate configured to be attached to a target portion of bone. In another embodiment, the system further includes a third cable link, wherein the first coupling member of the third cable link is configured to couple to the second coupling member of the second cable link such that the first, second and third cable links form a cable belt. In another embodiment, the system further includes a cable crimp coupled to the proximal end of the cerclage cable. In a further embodiment, the first and second coupling members are hooks. In another embodiment, the first and second cable links are pivotable relative to one another.

In another aspect, a method for securing a target portion of bone includes making an incision adjacent to the target portion of bone and passing a cerclage device through the incision and around the target portion of bone. The cerclage device includes a cable link including an upper surface and a bone-facing surface and extending from a first end to a second end. The cable link includes a through-hole extending therethrough from the first end to the second end, the through-hole sized and shaped to receive a cerclage cable therethrough. The first end includes a first coupling member and the second end includes a second coupling member. The cerclage device also includes an elongated cerclage cable slidably disposed within the through-hole, the elongated cerclage cable extending from a proximal end to a distal end and configured to circle the target portion of bone. The method also includes applying tension to a distal end of the cerclage cable to pull the cerclage device into a target position about the bone. The method also includes locking the cerclage device in the target position about the target portion of bone. In one embodiment, the first coupling member of a first cable link is configured to couple to the second coupling member of an adjacent second cable link such that the through-holes of the first and second cable links align to form an elongated cerclage cable passageway. In an embodiment, the first and second cable links are pivotable relative to one another. In another embodiment, the cerclage device includes a third cable link, wherein the first coupling member of the third cable link is configured to couple to the second coupling member of the second cable link such that the first, second and third cable links form a cable belt. In a further embodiment, the first coupling member is formed as at least one rounded protrusion configured to be slidably received by the second coupling member. In another embodiment, the second coupling member is formed as at least one C-shaped extension configured to slidably receive the first coupling member therein.

BRIEF DESCRIPTION

FIG. 1 shows a perspective view of a cable saddle system according to an exemplary embodiment;

FIG. 2A shows a perspective view of a cable saddle according to an exemplary embodiment;

FIG. 2B shows a top view of the cable saddle of FIG. 2A;

FIG. 2C shows a bottom view of the cable saddle of FIG. 2A;

FIG. 2D shows a side view of the cable saddle of FIG. 2A;

FIG. 2E shows a front view of the cable saddle of FIG. 2A;

DETAILED DESCRIPTION

Figure 3:
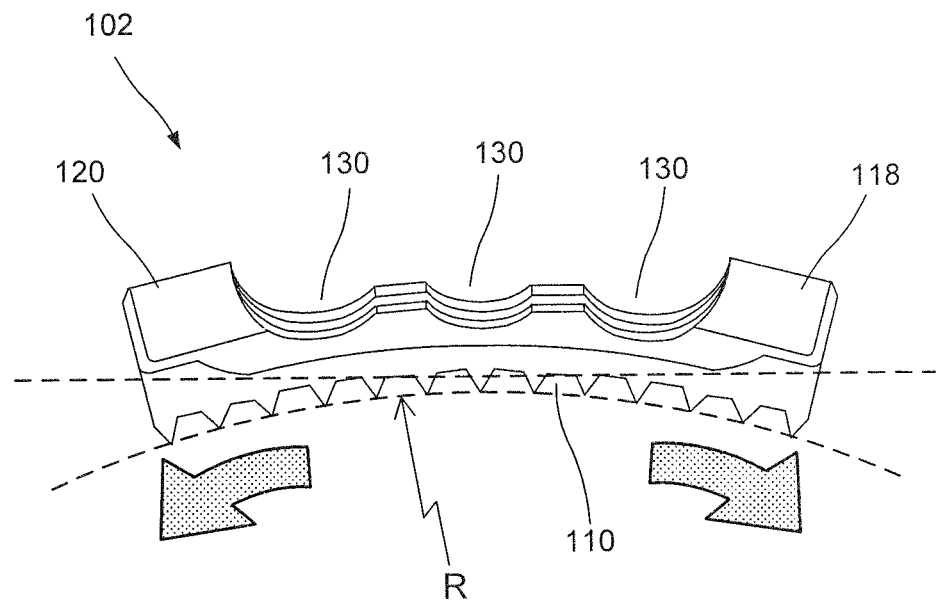
FIG. 3 shows another side view of the cable saddle of FIG. 2A.

The present embodiments may be further understood with reference to the following description and the appended drawings, wherein like elements are referred to with the same reference numerals. The present embodiments relate generally to methods and devices for the stabilization and fixation of fractured bones and bone fragments via a minimally invasive cerclage belt system. In particular, the present embodiments relate to methods and devices for securing a bone plate against a target portion of bone using a cerclage cable and cable saddle. The present embodiments also contemplate a cerclage cable belt comprising a plurality of belt links. The present embodiments may also be employed with any of a plurality of treatment procedures involving cerclage. As used in the application, the terms proximal and distal refer to a direction along the cerclage cable with a first end of the cable being identified as the proximal end and a second end of the cable being identified as distal. Components of an exemplary cable saddle according to the present embodiments will be described in relation to the direction which the cable passes therethrough. For example, an opening to a lumen into which a distal end of the cable is inserted and against which a proximal end of the cable is held will be described as the proximal opening of the lumen. The opposite end of the lumen from which the distal end of the cable exits will be described as the distal opening of the lumen and the other elements of the saddle will be similarly identified.

Figure 4:
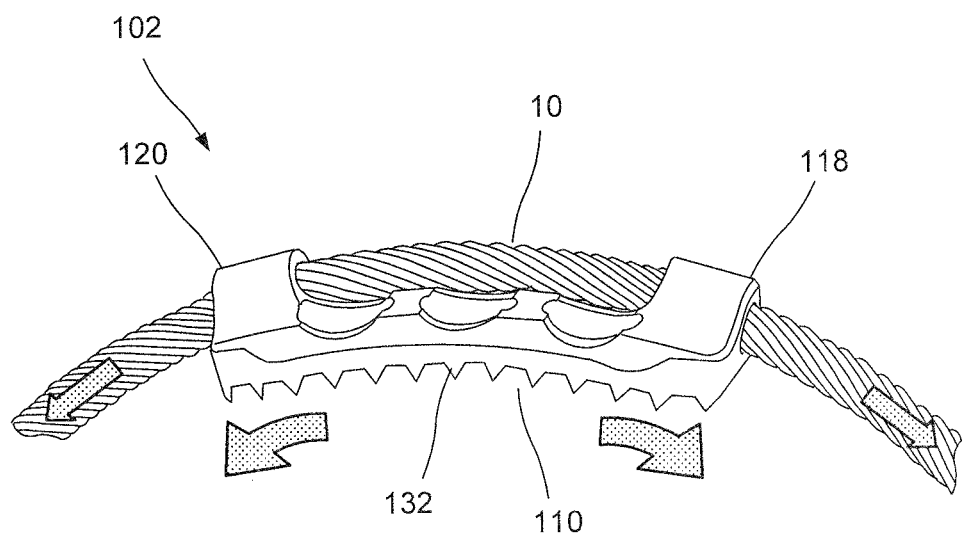
FIG. 4 shows a side view of the cable saddle and cable of the cable saddle system of FIG. 1.

As shown in FIGS. 1-4, a cable saddle system 100 according to a first exemplary embodiment comprises a saddle 102 for receiving a cable 10 to be looped around a bone plate 104 positioned on a target portion of bone 106. The saddle 102 comprises a saddle body 108 including a first bone-facing surface 110 which may be flat or contoured to and a second upper surface 112 extending between a first end 114 a second end 116 substantially parallel to one another. The saddle 102 includes a first loop 118 extending from the upper surface 112 at the first end 114 and a second loop 120 extending from the upper surface 112 at the second end 116. The first and second loops 118, 120 define first and second apertures 122, 124, respectively, extending therethrough. The diameters of the first and second apertures 122, 124 are substantially equal to one another and are selected to permit slidable insertion of the cable 10 therethrough with minimal lateral movement of the cable 10 therein. Specifically, the diameter of the first and second apertures 122, 124 is substantially equal to an outer diameter of the cable 10 plus a small clearance to permit the cable 10 to slide smoothly therethrough. While two loops 118, 120 are used in the present embodiment, as would be understood by those skilled in the art that any number of loops may be used so long as the cable 10 is constrained to lie over the saddle 102 so that the portion extending between the apertures does not lie directly on the bone. In an exemplary embodiment, upper surface 112 includes a semi-circular groove 126 extending from the first loop 118 to the second loop 120 and open to apertures 122, 124 sized to receive the portion of the cable 10 extending between the apertures 122, 124. The groove 126 holds the cable 10 in place to resist lateral movement of the cable 10 and helps the cable 10 to hold the saddle 102 against the target portion of bone 106 when cable tension is applied. The saddle 102 further includes a plurality of holes 128 extending from the bone-facing surface 110 to the upper surface 112. The holes 128 allow bony and soft tissue ingrowth into the saddle 102 to enhance long-term fixation and stability of the position of the saddle 102 on the bone while also reducing material mass. In an exemplary embodiment shown in FIGS. 2A-2C, six circular holes 128 are used. However, as those skilled in the art will understand, any shape and a number of holes 128 may be used so long as the structural integrity of the saddle 102 is maintained. For example, in another exemplary embodiment shown in FIG. 5A four elongated holes 128' are shown. The upper surface 112 includes a plurality of cutouts or reliefs 130 extending generally transverse to the groove 126 (i.e., transverse to a longitudinal axis L of the saddle 102). The reliefs 130 allow the saddle 102 to bend and flex to more easily conform to the contour of the target bone 106, as can be seen in FIGS. 3-4. In an exemplary embodiment, the reliefs 130 overlap with the holes 128 to further enhance the flexibility of the saddle 102 and to reduce material mass. It will be understood that any number of reliefs 130 may be used. For example, as can be seen in FIG. 2B, three reliefs 130 are disposed on the upper surface 112 extending transverse to the longitudinal axis L of the saddle 102 and passing over two holes 128 each, one hole 128 on either side of the longitudinal axis L of the saddle body 108. It will be understood by those skilled in the art that any configuration of reliefs 130 and holes 128 may be used as necessary to achieve the desired flexibility of the saddle 102. As shown in FIGS. 2C-2D, the bone-facing first surface 110 includes ribs or ridges 132 extending therefrom to increase a grip of the saddle body 108 on the bone and to prevent undesired movement of the saddle body 108 relative to the target bone 106 after the saddle body 108 has been placed in a desired position.

As would be understood by those skilled in the art, the saddle body 108 may be formed to include the loops 118, 120, groove 126, holes 128, reliefs 130 and ridges 132 using conventional manufacturing methods such as welding, pressing, electrical discharge machining, casting, machining and/or forging. Saddle 102 may be formed of a metal such as stainless steel or titanium. Additionally, the bone-facing surface 110 may be coated or further roughened to enhance the grip of the saddle 102 on the target bone 106.

In an exemplary method, target portions of bone (not shown) are initially moved relative to one another into a desired corrective position (e.g. by reducing a fracture) prior to insertion of the cable 10 and the saddle 102 to desired positions relative to the target portions of bone. In an exemplary embodiment, once the target portions of bone have been positioned as desired, a bone plate 104 may be inserted (e.g., through a minimally invasive incision adjacent to the target portions of bone 106) and fixed to the target portions of bone to maintain the target portions of bone in a desired spatial arrangement. In another exemplary embodiment, no bone plate is used. Once the bone plate 104 has been positioned as desired, the cable 10 may then be inserted through the same minimally invasive incision and wound around the target portions of bone 106 to further stabilize the positions of the target portions of bone. The distal end of the cable 10 is then threaded through the first and second loops 118, 120 of the cable saddle 102 and the cable 10 is used to move the saddle 102 over the bone to a desired position. In an exemplary embodiment, the saddle 102 is positioned on a surface of the bone opposite the bone plate 104, as seen in FIG. 1. When the cable 10 is tightened around the target bone 106, the saddle 102 increases the surface area over which the compressive force from the cable 10 is exerted on the bone reducing the risk that the cable 10 will dig or subside into the bone. The cable 10 is then tensioned to a desired level as would be understood by those skilled in the art so that a desired force is applied to the bone. As the desired force is being applied to the cable 10, the cable 10 compresses the first and second ends 114, 116 of the saddle body 108 against the bone 106, bending the saddle body 108 to adapt to a contour of the bone 106. The cable 10 is then locked in place using, for example, a cable crimp 134. After the cable 10 has been locked in place, any extra length of the cable 10 extending from the crimp 134 is cut. It will be understood by those skilled in the art that multiple cables 10 and cable saddle 102 may be used to treat the fractured bone.

Figure 5A:
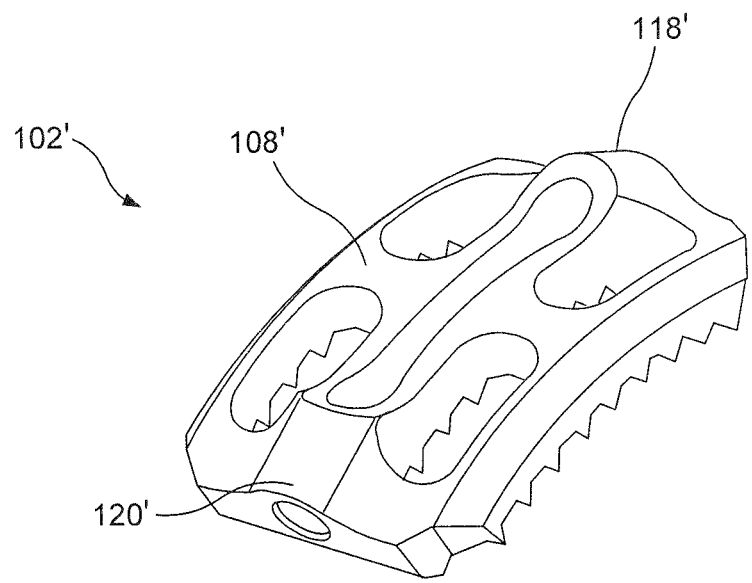
FIG. 5A shows a perspective view of a cable saddle according to a second exemplary embodiment.
Figure 5B:
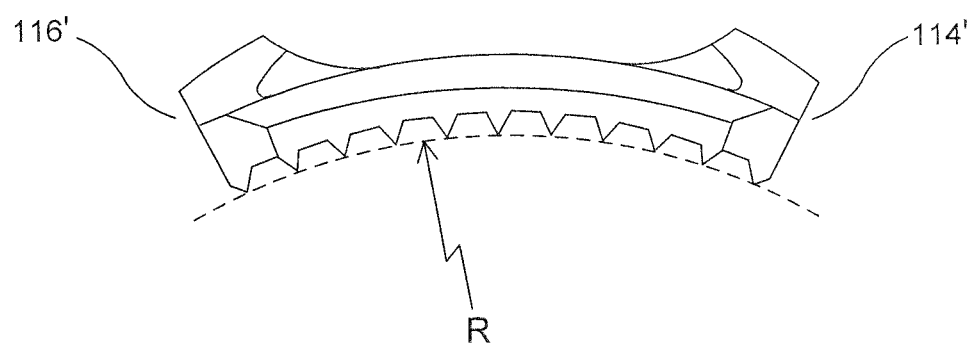
FIG. 5B shows a side view of the cable saddle of FIG. 5A.

As shown in FIGS. 5A and 5B, a system 100' according to an alternate embodiment is substantially similar to the system 100 described above, comprising a cable saddle 102' including a body 108' having two loops 118', 120' through which a cable (not shown) is slidably received. The configuration of the cable saddle 102' is the same as that of the cable saddle 102 except, rather than having a substantially flat body, saddle body 108' is pre-contoured to conform to a shape of the outer surface of the target bone (not shown). Specifically, the saddle body 108' is curved along its length from a first end 114' to a second end 116' such that first bone-facing surface 110' has a radius of curvature, R, corresponding generally to a contour of a target surface of the bone. Because the saddle 102' is pre-contoured to match a contour of a surface of the bone, the increased flexibility of the saddle body 108 is not as critical to the functioning of the saddle body 108'. Thus, the upper surface 112' of the embodiment shown in FIGS. 5A-5B does not include the reliefs in upper surface 112' as were present in the saddle body 108. However, it will be understood that cable saddle 102' may include reliefs if further bending and/or flexibility of the cable saddle 102' is required.

Figure 6:
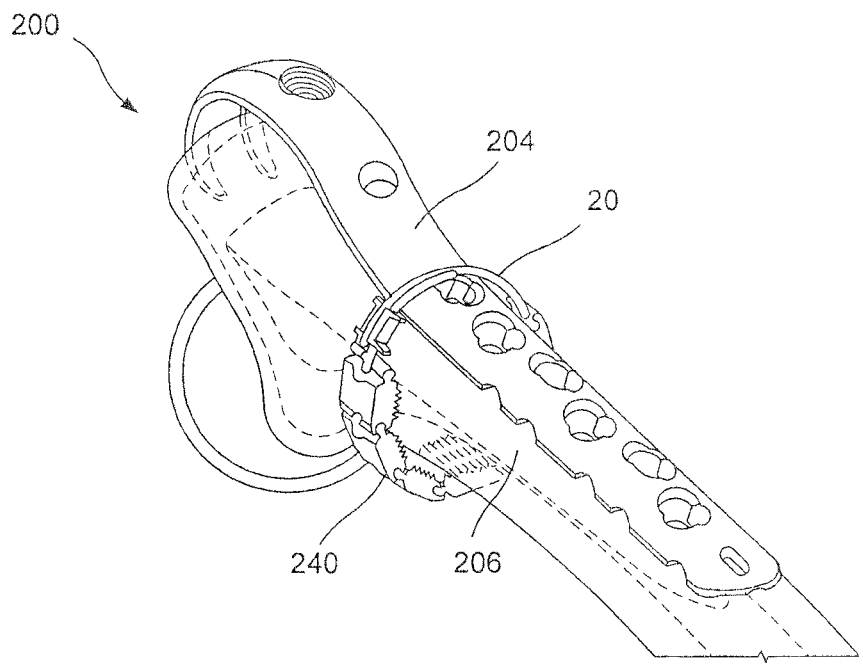
FIG. 6 shows a perspective view of a cable belt system according to an exemplary embodiment.
Figure 7:
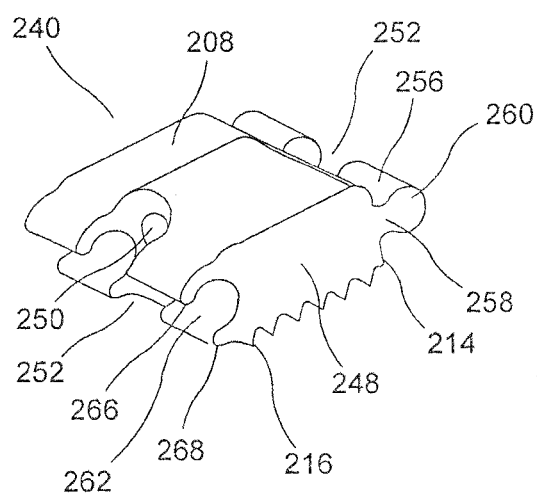
FIG. 7 shows a perspective view of a cable link of the cable belt system of FIG. 6.
Figure 8:
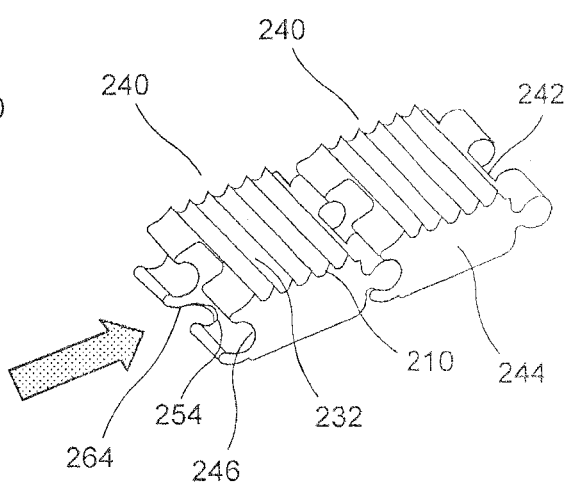
FIG. 8 shows a perspective view of a interlocked pair of cable links of the belt system of FIG. 6.
Figure 9:
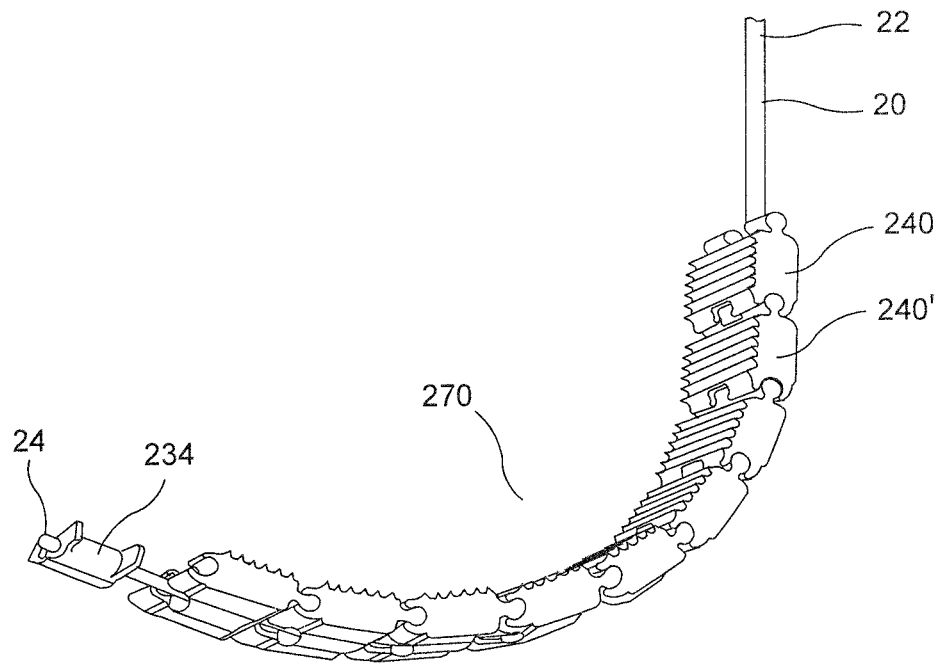
FIG. 9 shows a perspective view of a cable belt of the cable belt system of FIG. 6.

As shown in FIGS. 6-10, a cable belt system 200 according to an exemplary embodiment comprises a plurality of cable links 240 for receiving an elongated cerclage cable 20 to be looped around a bone plate 204 positioned on a target portion of bone 206. Each cable link 240 includes a body 208 extending along a longitudinal axis from a first end 214 to a second end 216 and having a first bone-facing surface and a second surface connected by four side-walls 242, 244, 246, 248. A central longitudinal through-hole 250 extends through the cable link body 208 along the longitudinal axis from a first side wall 242 to a second side wall 246. The diameter of the through-hole 250 is selected to permit slidable insertion of the cerclage cable 20 therethrough with minimal lateral movement of the cable 20 within. Specifically, the diameter of the through-hole 250 is substantially equal to an outer diameter of the cable 20 plus a small clearance to permit the cable 20 to slide smoothly therethrough. Each cable link 240 is configured to interlock with one or more other cable links 240' through a male connector 252 at first end 214 and a female receiving connector 254 at second end 216. Specifically, the cable link 240 includes a male connection portion 252 comprising a pair of protrusions 256 extending from a first end 214 of the body 208. The protrusions 256 are positioned on either side of the central through-hole 250 and extend from a first side wall 242. Each of the protrusions 256 includes a connecting portion 258 and a rounded head portion 260. Each head portion 260 in this embodiment is substantially cylindrical and extends along an axis substantially perpendicular to the longitudinal axis of the cable link 240. Each rounded head portion 260 is sized to laterally slide into a corresponding rounded receiving space 262 of a female connection portion 254, as shown in FIG. 8. That is, the diameters of rounded head portions 260 are selected to permit slidable insertion of the head portions 260 into the female connection portion 254.

The female connection portion 254 comprises a pair of C-shaped extensions 264 extending from the second end 216 of the body 208. The extensions 264 are positioned on either side of the central through-hole 250 and include an upper curved portion 266 and a lower curved portion 268 extending from second side wall 244 to define a receiving space 262 therebetween. When connected with the protrusions 256 of a second cable link 240, the upper and lower curved portions 266, 268 extend substantially around the head portion 260 of the protrusions 256 such that the protrusions 256 are unable to be pulled out of the receiving space 262. The diameter of the receiving space 262 is selected to permit slidable insertion of the protrusions 256 of the male connection portion 252 therethrough while also allowing the protrusions 256 to pivot in a plane perpendicular to the longitudinal axis of the cable links 240. Specifically, the diameter of the receiving space 256 is substantially equal to an outer diameter of the protrusions 256 plus a small clearance to permit the protrusions 262 to slide smoothly therethrough and pivot while held within the extensions 264. The cable links 240 are configured such that, when two or more links 240 are coupled to one another, the through-holes of each adjacent cable link 240 align with one another to form an elongated passageway for the cable 20. In an operative configuration, a distal end 22 of the cable 20 is inserted through a proximal end of a first through hole 250 and drawn distally through each of the interlocked cable links 240. The cable 20, once threaded through each cable link 240, further prevents uncoupling of the cable links 240 by limiting lateral movement of the links 240 relative to one another while a series of cable links 240 may then hold the entire circumference of the cable 20 out of contact with the bone.

As shown in FIGS. 7-8, the bone-facing first surface 210 includes ribs or ridges 232, similar to the ridges 132, to increase grip against the bone and to prevent movement when in contact with the target bone 206 while also increasing contact surface area to prevent the links 240 from sinking into the bone 206.

Figure 10:
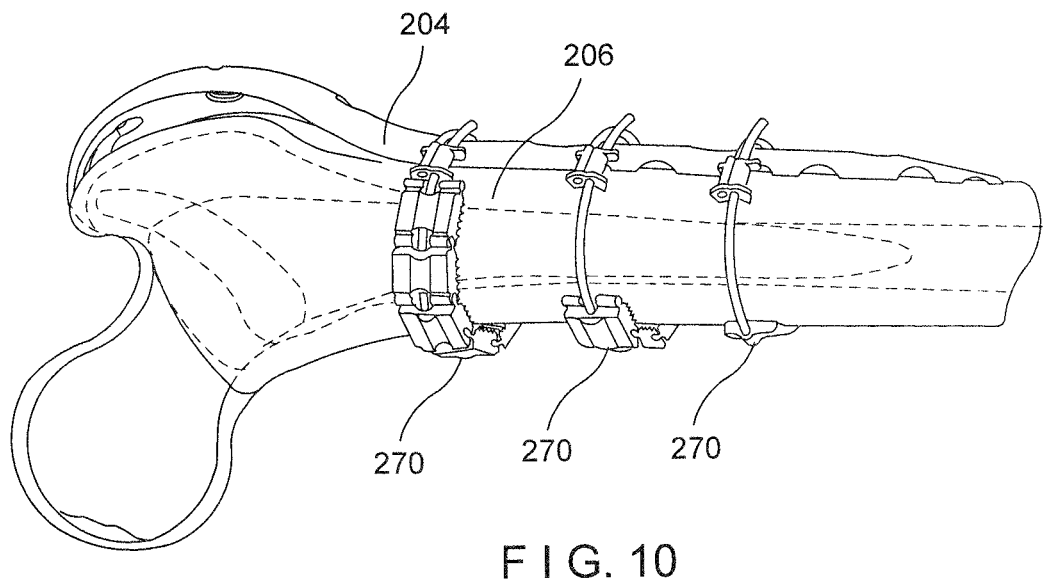
FIG. 10 shows another perspective view of the cable belt system of FIG. 6.

In an exemplary method, a number of cable links 240 selected to extend around a desired portion of a circumference of a target portion of bone are initially linked together by sliding each of the male connector portion 252 through the receiving portions 262 of the female connector portion 254 to create a chain, or belt, 270 of cable links 240. Once the desired number of cable links 240 has been coupled together, distal end 22 of cable 20 is inserted through each of the adjacent through-holes 250 of the interlocked cable links 240 prior to surgery. In an exemplary embodiment, a proximal end 24 of the cable 20 includes an increased diameter stop member (not shown) at a proximal end to prevent the cable links 240 from sliding off of the cable 20. In another exemplary embodiment, the proximal end 24 of the cable 20 includes a cable crimp 234 preventing the cable links 240 from sliding off of the cable 20. During surgery, as those skilled in the art will understand, target portions of bone (not shown) are moved relative to one another into a desired corrective position (e.g., by reducing the fracture) prior to insertion of the cable 20 and cable links 240 into the body. In an exemplary embodiment, once the target portions of bone have been positioned as desired, a bone plate 204 is inserted through a minimally invasive incision adjacent to the target portions of bone 206 and fixed to the target portions of bone to fix these portions of bone in a desired spatial relation to one another. In another exemplary embodiment, no bone plate is used. Once the bone plate 204 is in position, the distal end 22 of the cable 20 is inserted through the same minimally invasive incision and wound around the target portions of bone 206 to hold the bone together. As the cable 20 is wound about the target bone 206, the cable 20 tows the cable link belt 270 around the target bone 206 so that the further cable 20 is pulled around the bone, the further the cable belt 270 is also pulled about the bone towards a target position encircling a target circumference of the target bone 206. In an exemplary embodiment, the cable belt 270 extends over a target portion of a surface of the bone (e.g., a portion diametrically opposite the bone plate 204) as can be seen in FIG. 6. Thus, as the cable 20 is tightened around the target bone 206, the cable belt 270 holds this portion of the cable 20 out of direct contact with the bone and spreads the compressive force exerted by the cable 20 over a larger surface area preventing the cable 20 from digging or subsiding into the bone. The cable 20 is tensioned to a desired level as would be understood by those skilled in the art to apply a desired compressive force to the bone. As the desired force is being applied to the cable 20, the cable 20 presses the cable belt 270 against the target bone 206, causing the male connection portions 252 to pivot within the female connection portions 254 so that the cable belt 270 contours to the shape of the bone 206. The cable 20 is then locked in place using, for example, a cable crimp 234. After the cable 20 has been locked in place at the desired tension, any extra length of the cable 20 extending from the crimp 234 is cut. It will be understood by those skilled in the art that multiple cable belts 270 of varying lengths may be used to treat the fractured bone, as shown in FIG. 10.

Figure 11:
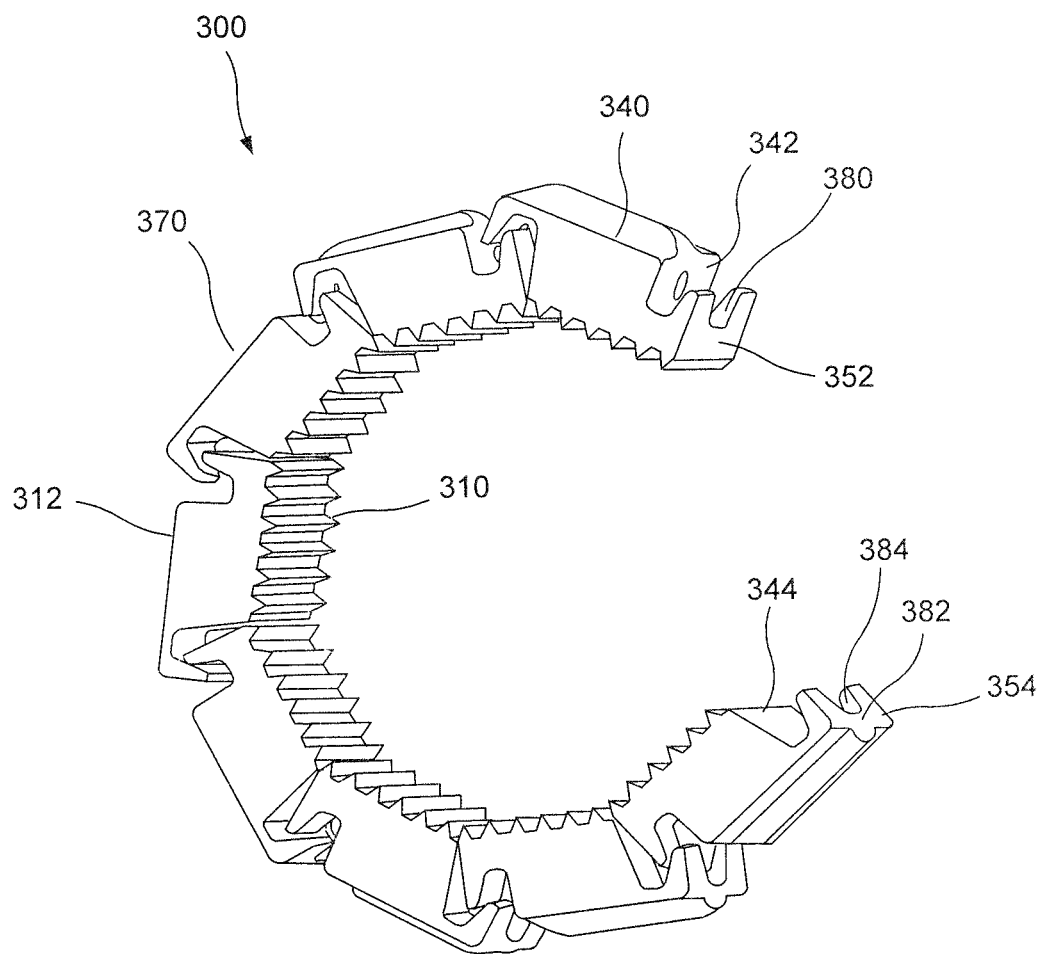
FIG. 11 shows a perspective view of a cable belt according to another exemplary embodiment.

As shown in FIG. 11, a cable belt system 300 according to a further embodiment is substantially the same as system 200 described above, comprising a cable belt 370 formed of a plurality of cable links 340 coupled together at connection portions 352, 354. However, in this embodiment, the connection portions are configured as interlocking hooks 380, 382 extending from each of the first and second side walls 342, 344. A first hook 380 extends from first side wall 342 adjacent to the bone-facing surface 310 towards the upper surface 312 while the second hook 382 extends from the second side wall 344 adjacent to the upper surface 312 toward the bone-facing surface 310 such that, the links 340 are coupled to one another by interlocking the first and second hooks 380, 382, as shown in FIG. 11. Each of the hooks 380, 382 includes a substantially semi-circular cutout 384 which aligns with a corresponding through-hole 350 of the cable link 340 to allow free passage of the cable 30 through links 340. Specifically, the cutouts 384 are sized to be equal to an outer diameter of the cable 30 plus a small clearance to permit the cable 30 to slide smoothly therethrough. As would be understood by those skilled in the art, the connection portions 352, 354 of the cable links 340 may be configured in any other suitable way to allow free passage of the cable 30 and pivoting movement of the cable links 340 relative to one another so to permit the cable belt 370 to conform to the shape of an outer surface of the target portion of bone when the cable 30 is tightened therearound.

It will be apparent to those skilled in the art that various modifications and variations may be made in the structure and the methodology of the present embodiments, without departing form the spirit or scope of the embodiments. Thus, it is intended that the present embodiments cover modifications and variations provided that they come within the scope of the appended claims and their equivalents.

What is claimed is:

1. A bone fracture stabilization device, comprising:
   a body extending from a first end to a second end along a longitudinal axis, the body defining an upper surface and a bone facing surface and including a first loop extending from the upper surface at the first end and a second loop extending from the upper surface at the second end, the first and second loops including apertures extending therethrough and sized and shaped to receive a cerclage cable therethrough from the first loop to the second loop along the longitudinal axis of the body, the upper surface including a plurality of elongated reliefs extending in a direction transverse to the longitudinal axis of the body to facilitate bending of the body along its longitudinal axis to conform to a contour of a target portion of bone;
   wherein the upper surface includes a groove extending from the first loop to the second loop and wherein the groove is open to the apertures.

2. The device of claim 1, wherein the bone facing surface includes a plurality of ridges.

3. The device of claim 1, wherein the body includes a plurality of holes extending from the bone facing surface to the upper surface.

4. The device of claim 3, wherein a first one of the reliefs is open to a first one of the holes.

5. The device of claim 1, wherein the bone facing surface is contoured to correspond to a contour of the target portion of bone.

6. The device of claim 1, wherein the first and second loops are formed integrally with the body.

7. A system for stabilizing a bone fracture, comprising:
   a body extending from a first end to a second end along a longitudinal axis, the body defining an upper surface and a bone facing surface opposite the upper surface, wherein the body includes a first loop extending from the upper surface at the first end and a second loop extending from the upper surface at the second end, the first and second loops including apertures extending therethrough sized and shaped to receive a cerclage cable therethrough from the first loop to the second loop along the longitudinal axis of the body, the upper surface of the body including a plurality of elongated reliefs extending in a direction transverse to the longitudinal axis of the body to facilitate bending of the body along its longitudinal axis to conform a shape of the body to a contour of a first target portion of bone;
   wherein the upper surface includes a groove extending from the first loop to the second loop and wherein the groove is open to the apertures; and an elongated bone plate configured to be attached to a second target portion of bone.

8. The system of claim 7, further comprising a cable crimp configured to lock the cerclage cable in place.

9. The system of claim 7, wherein the body is configured to be positioned on a first surface of bone and the elongated bone plate is configured to be positioned on a second surface of bone laterally opposite the first surface of bone.

10. The system of claim 7, wherein the bone facing surface of the body includes a plurality of ridges formed thereon.

11. The system of claim 7, wherein the body includes a plurality of holes extending therethrough from the bone facing surface to the upper surface thereof.

12. The system of claim 11, wherein a first one of the reliefs is open to a first one of the holes.

13. The system of claim 7, wherein the first and second loops are formed integrally with the body.

* * * * *